(12) United States Patent
Denzinger et al.

(10) Patent No.: US 12,190,503 B2
(45) Date of Patent: Jan. 7, 2025

(54) METHOD AND SYSTEM FOR DETERMINING A SIGNIFICANCE SCORE ASSOCIATED WITH A MEDICAL IMAGING DATASET OF A PATIENT

(71) Applicant: Siemens Healthineers AG, Forchheim (DE)

(72) Inventors: Felix Denzinger, Nuremberg (DE); Michael Wels, Bamberg (DE); Max Schoebinger, Hirschaid (DE); Alexander Muehlberg, Nuremberg (DE); Michael Suehling, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 665 days.

(21) Appl. No.: 17/477,839

(22) Filed: Sep. 17, 2021

(65) Prior Publication Data

US 2022/0092775 A1    Mar. 24, 2022

(30) Foreign Application Priority Data

Sep. 24, 2020    (EP) .................................. 20198169

(51) Int. Cl.
*G06T 7/00*        (2017.01)
*A61B 6/00*        (2024.01)
(Continued)

(52) U.S. Cl.
CPC ........ *G06T 7/0012* (2013.01); *G06F 18/2148* (2023.01); *G06T 7/11* (2017.01); (Continued)

(58) Field of Classification Search
None
See application file for complete search history.

(56) References Cited

U.S. PATENT DOCUMENTS

| 11,309,071 B2 * | 4/2022 | Anderson | A61B 6/032 |
| 2022/0000441 A1 * | 1/2022 | Yang | A61B 6/504 |
| 2022/0215542 A1 * | 7/2022 | Paul | G16H 50/20 |

FOREIGN PATENT DOCUMENTS

| CN | 111445449 B | * | 3/2024 | ............ G06F 18/24 |
| KR | 102354396 B1 | * | 5/2020 | |

OTHER PUBLICATIONS

Cury et al.:"CAD-RADST™: Coronary Artery Disease—Reporting and Data System.: An Expert Consensus Document of the Society of Cardiovascular Computed Tomography (SCCT), the American College of Radiology (ACR) and the North American Society for Cardiovascular Imaging (NASCI). Endorsed by the American College of Cardiology" IJ Am Coll Radiol 1312 Pt A):1458-1466).

(Continued)

*Primary Examiner* — Mohammed Rachedine
(74) *Attorney, Agent, or Firm* — Harness, Dickey & Pierce, P.L.C.

(57) ABSTRACT

A method, preferably a computer implemented method, and system are for providing output data associated with a medical imaging dataset of a patient, the medical imaging dataset including image data of a region of an anatomy of a patient including a plurality of coronary arteries. The output data is a significance score associated with a medical imaging data set of a patient. The method, in the most general terms, includes receiving input data, e.g. via a first interface, generating output data by applying algorithmic operations to the input data, and providing the output data, e.g. via a second interface.

20 Claims, 3 Drawing Sheets

(51) Int. Cl.
    *A61B 6/03*     (2006.01)
    *A61B 6/50*     (2024.01)
    *G06F 18/214*     (2023.01)
    *G06N 3/08*     (2023.01)
    *G06T 7/10*     (2017.01)
    *G06T 7/11*     (2017.01)
    *G06T 7/68*     (2017.01)
    *G16H 30/40*     (2018.01)
    *G16H 50/20*     (2018.01)

(52) U.S. Cl.
    CPC ............... *G06T 7/68* (2017.01); *G16H 30/40* (2018.01); *G16H 50/20* (2018.01); *G06T 2207/30101* (2013.01); *G06V 2201/03* (2022.01)

(56) References Cited

OTHER PUBLICATIONS

Muscogiuri et al.: Performance of a deep learning algorithm for the evaluation of CAD-RADS classification with CCTA. Atherosclerosis, 2020,294:25-32..-doi10.10106/j.atheriosclerosis.2019.12.001.

Zheng, Yefeng et al. "Robust and accurate coronary artery centerline extraction in CTA by combining model-driven and data-driven approaches" MICCAI 2013, Part III, LNCS 8151, pp. 74-81, 2013.

Klein Paul et at. "Method for Automated Coronary Tree Labeling Using Bidirectional Tree structured Recurrent Neural Networks"; published Jun. 27, 2019.

Austen Gerald W et al. "A reporting system on patients evaluated for coronary artery disease. Report of the Ad Hoc Committee for Grading of Coronary Artery Disease, Council on Cardiovascular Surgery, American Heart Association" in Circulation vol. 51, No. 4, Apr. 1, 1975, https://doi.org/10.1161/01.CIR.51.4.5.

Majd Zreik et al: "Automatic Detection and Characterization of Coronary Artery Plaque and Stenosis using a Recurrent Convolutional Neural Network in Coronary CT Angiography"; arxiv.org, Cornell University Library; 201 Olin Library Cornell University Ithaca; NY 14853; XP080870084.

Liu Jiang et al: "A Vessel-Focused 3D Convolutional Network for Automatic Segmentation and Classification of Coronary Artery Plaques in Cardiac CTA"; Advances in Databases and Information Systems, [Lecture Notes in Computer Science, Lect.Notes Computer], Springer, International Publishing, Cham, pp. 131-141; 2019.

Majd Zreik et al.: "A Recurrent CNN for Automatic Detection and Classification of Coronary Artery Plaque and Stenosis in Coronary CT Angiography"; arxiv.org, Cornell University Library, 201 Olin Library Cornell University Ithaca, NY 14853; 2018.

* cited by examiner

METHOD AND SYSTEM FOR
DETERMINING A SIGNIFICANCE SCORE
ASSOCIATED WITH A MEDICAL IMAGING
DATASET OF A PATIENT

Priority Statement

The present application hereby claims priority under 35 U.S.C. § 119 to European patent application number EP 20198169.3 filed Sep. 24, 2020, the entire contents of which are hereby incorporated herein by reference.

FIELD

Example embodiments of the invention generally relate to a method and system for determining a significance score associated with a medical imaging dataset of a patient.

Example embodiments of the invention are in the field of medical imaging, which is used for of creating visual representations of the interior of a body for clinical analysis and medical intervention, as well as visual representation of the function of some organs or tissues. In particular, example embodiments of the invention are is in the field of blood vessel analysis by medical imaging.

For improved diagnosis and treatment planning, scores or classifications are assigned to an individual patient's manifestation of a pathophysiology or disease state.

Example embodiments of the invention generally relate to the assignment of a significance score for the analysis of blood vessels of a patient based on medical imaging data of the patient.

BACKGROUND

Coronary heart disease is one of the major causes of death worldwide. It is associated with atherosclerotic plaques that narrow the coronary arteries. One method of assessing and visualizing these plaque deposits and the corresponding stenosis in the coronary vessel structure is by analyzing medical imaging datasets from a medical imaging modality such as Computed Tomography (CT), in particular coronary CT angiography (CCTA) or magnetic resonance imaging (MR).

For further evaluation of a medical imaging dataset of a patient, it is useful to determine a significance score associated with a medical imaging dataset.

In daily clinical practice, the so-called CAD-RADS score (Coronary Artery Disease Reporting and Data System) determines recommended patient management after CCTA examinations (Cury, R. C., et al. (2016). "CAD-RADS: Coronary Artery Disease-Reporting and Data System: An Expert Consensus Document of the Society of Cardiovascular Computed Tomography (SCCT), the American College of Radiology (ACR) and the North American Society for Cardiovascular Imaging (NASCI). Endorsed by the American College of Cardiology." J Am Coll Radiol 13(2 Pt A): 1458-1466). In the majority of cases, this score is determined based on the most severe detected stenosis within the coronary tree of respective patient. However, this score is currently assessed manually by a human reader, which makes the procedure time-consuming and error-prone causing inter- and intra-observer variance to be high, in particular for non-expert radiologists.

CAD-RADS scores range from 0 to 5. With 0 referring to a patient with no plaque segments at all, all other CAD-RADS scores mostly refer to the highest stenosis lesion within the coronary tree which get categorized as minimal, mild, moderate, severe and total occlusion. Exceptions to this are lesions within the left main artery, which due to the importance of this vessel lead to a CAD-RADS score of 4 already if a moderate lesion is present.

Grades 3 and above suggest a further investigative workflow including functional and/or invasive assessment. Contrary to this, CAD-RADS scores of 2 and below require no further cardiac investigation.

Until now, qualitative assessment by eye-balling is the clinical standard.

Additionally, a method for the prediction of clustered CAD-RADS scores using a 2D convolutional neural network exists (Muscogiuri G, Chiesa M, Trotta M, et al. Performance of a deep learning algorithm for the evaluation of CAD-RADS classification with CCTA. Atherosclerosis. 2020; 294:25-32. doi:10.1016/j.atherosclerosis.2019.12.001). In their work they reformat the CCTA scan to a 2D grid and classify based on this representation. Therefore, it does not require prior preprocessing steps. However, the network decision cannot be tracked to the location of the culprit lesion in their approach, and also their approach lacks a representation of the coronaries. For an AI-based approach to be clinically feasible the decision of the approach needs to be explainable to a certain degree. Further, this prior art method is not able to reach a level of performance which allows for a clinical application and is limited to a clustered version of the score.

SUMMARY

At least one embodiment of the invention is directed to achieving an improved determination of a significance score based on medical imaging data in an automated fashion.

In the following, embodiments of the invention are described with respect to systems as well as with respect to methods. Elements, characteristics, advantages or alternative embodiments herein can be assigned to the other objects and vice versa. In other words, embodiments and claims for the providing systems can be improved with features described or claimed in the context of the methods and vice versa. In this case, the functional features of the method are embodied by objective units of the providing system. Furthermore, elements, characteristics, advantages or alternative embodiments described in connection with particular example embodiments can be assigned to the invention in its most general terms.

In its most general terms, at least one embodiment of the invention relate to a method, preferably a computer implemented method, for providing output data. The output data is a significance score associated with a medical imaging data set of a patient. The method of the invention, in the most general terms comprises the steps of receiving input data, e.g. via a first interface, generating output data by applying algorithmic operations to the input data, providing the output data, e.g. via a second interface.

In its most general terms, at least one embodiment of the invention further relates to a system, comprising a first interface, configured for receiving input data, a second interface, configured for providing output data, a computation unit, configured for applying algorithmic operations to the input data, wherein the output data is generated.

In its most general terms, at least one embodiment of the invention further relates to a computer program comprising instructions which, when the program is executed by a computer cause the computer to carry out at least one embodiment of the method of invention in its most general terms.

In its most general terms, at least one embodiment of the invention further relates to a computer-readable medium comprising instructions which, when executed by a computer cause the computer to carry out at least one embodiment of the method of invention in its most general terms.

According to an example embodiment, the invention relates to a method of determining a significance score associated with a medical imaging dataset of a patient, the medical imaging dataset comprising image data of a region of a patient's anatomy including a plurality of coronary arteries; comprising:

Receiving the medical imaging data set;

Automatically partitioning each coronary artery of the plurality of coronary arteries into one or more coronary artery segments;

For each coronary artery segment, extracting a representation of a corresponding section of the coronary artery from the medical imaging data set;

For each coronary artery segment, extracting one or more features from the representation of the corresponding section of the coronary artery;

Performing a combining operation based on the extracted features for all of the coronary segments (of the the one or more coronary artery segments) to obtain a global set of features based on the quantitative information for each coronary segment;

Determining the significance score based on the global set of features; and

Outputting the determined significance score.

In particular, an embodiment of the invention further relates to a system for determining a significance score associated with a medical imaging dataset of a patient, the medical imaging dataset comprising image data of a region of a patient's anatomy including a plurality of coronary arteries; comprising:

A first interface for receiving unit for receiving the medical imaging data set;

A partitioning unit for automatically partitioning each coronary artery of the plurality of coronary arteries into one or more coronary artery segments;

A first extraction unit for extracting a representation of a corresponding section of the coronary artery from the medical imaging data set;

A second extraction unit for extracting a one or more features from the representation of the corresponding section of the coronary artery, A combining unit for performing a combining operation based on the extracted features for all of the coronary segments to obtain a global set of features based on the quantitative information for each coronary segment;

A calculation unit for determining the significance score based on the global set of features; and A second interface for providing the determined significance score.

An embodiment of the invention further relates to a computer program, which performs the steps of the methods of an embodiment of the invention if the computer program is executed on an evaluation device which may be or may comprise a computer or may be comprised by a computer.

An embodiment of the invention further relates to an electronically readable storage medium, on which the computer program of an embodiment of the invention is stored.

An embodiment of the invention further relates to a method of determining a significance score associated with a medical imaging dataset of a patient, the medical imaging dataset including image data of a region of an anatomy of a patient including a plurality of coronary arteries, the method comprising:

receiving the medical imaging data set;

automatically partitioning each coronary artery of the plurality of coronary arteries, into one or more coronary artery segments;

extracting, for each respective coronary artery segment, a respective representation of a corresponding section of the respective coronary artery of the plurality of coronary arteries, from the medical imaging data set;

extracting, for each respective coronary artery segment, one or more features from the respective representation of the corresponding section of the coronary artery;

performing a combining operation based on the one or more features extracted for all of the respective coronary segments to obtain a global set of features based on quantitative information for each respective coronary segment;

determining the significance score based on the global set of features; and outputting the significance score determined.

An embodiment of the invention further relates to a system for determining a significance score associated with a medical imaging dataset of a patient, the medical imaging dataset including image data of a region of an anatomy of a patient including a plurality of coronary arteries, the system comprising:

a first interface to receive the medical imaging data set;

a partitioning unit to automatically partition each respective coronary artery of the plurality of coronary arteries into one or more coronary artery segments;

a first extraction unit to extract a representation of a corresponding section of the respective coronary artery from the medical imaging data set;

a second extraction unit to extract a one or more features from the representation of the corresponding section of the respective coronary artery;

a combining unit to perform a combining operation, based on features extracted for all of the one or more coronary segments to obtain a global set of features based on respective quantitative information for each respective coronary segment;

a calculation unit to determine the significance score based on the global set of features; and a second interface to provide the significance score determined.

An embodiment of the invention further relates to a non-transitory computer program product, storing a computer program to perform the method of an embodiment upon the computer program being executed on an evaluation device.

An embodiment of the invention further relates to a non-transitory electronically readable storage medium, storing a computer program to perform the method of an embodiment upon the computer program being executed on an evaluation device.

BRIEF DESCRIPTION OF THE DRAWINGS

Further details and advantages of the current invention can be taken from the following description of example embodiments in conjunction with the drawings in which.

Figure 1:
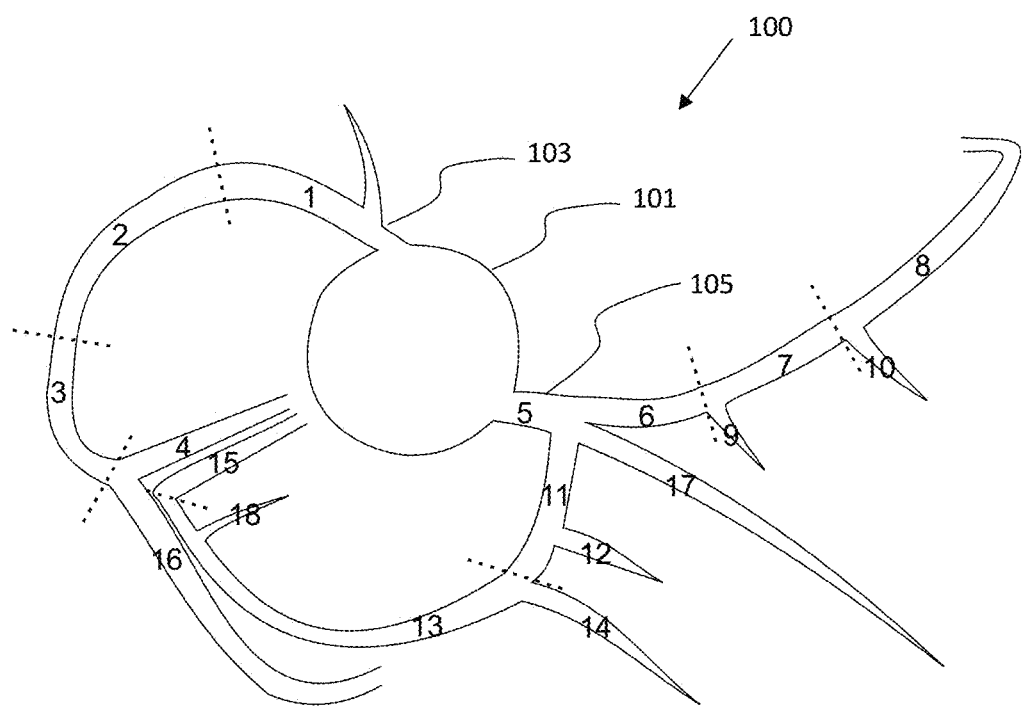
FIG. 1 shows a schematic representation of coronary arteries.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion.

In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In its most general terms, at least one embodiment of the invention relate to a method, preferably a computer implemented method, for providing output data. The output data is a significance score associated with a medical imaging data set of a patient. The method of the invention, in the most general terms comprises the steps of receiving input data, e.g. via a first interface, generating output data by applying algorithmic operations to the input data, providing the output data, e.g. via a second interface.

The input data in its most general terms is a medical imaging data set. The medical imaging data set is based on an image acquisition of a medical imaging device or modality such as CT, MR, ultrasound or other suitable medical imaging device or modality. Further, the medical imaging data set comprises imaging data derived from an image acquisition of a region of a patient's body or anatomy comprising a plurality of blood vessels, in particular a plurality of coronary arteries. The medical imaging data may comprise a raw data set, a reconstructed image data set, and/or an image data set which has been further processed after reconstruction. The medical imaging data set may comprise further data, such as segmentation data and data derived from segmentation data, such as identification data related to a segmented structure within the medical imaging data set. Image segmentation is the process of partitioning a digital image into multiple segments (sets of pixels, also known as image objects). The goal of segmentation is to simplify and/or change the representation of an image into something that is more meaningful and easier to analyze, and allows the analysis of anatomic structure, such as blood vessels. For example, and with regard to coronary arteries, data derived from segmentation data may comprise identification data of individual coronary arteries (e.g. such as the major coronary arteries, the right coronary artery (RCA), left circumflex artery (LCX) and left anterior descending (LAD)). The data derived from segmentation data may further comprise blood vessel centerline data. The medical imaging data set may comprise further data such as metadata, wherein the metadata may comprise patient identification information, clinical information, e.g. on previous diagnoses, disease status, etc., scan information, e.g. based on the used medical imaging device or modality, setting of the medical imaging device or modality used for acquiring the scan or the medical imaging data set and so on.

In describing an embodiment of the invention in its most general terms, the step of generating output data by applying algorithmic operations to the input data comprises the steps of partitioning each blood vessel comprised by the medical imaging data set of the plurality of blood vessels into one or more blood vessel segments (such that altogether a plurality of blood vessel segments is obtained);

For each blood vessel segment, extracting a representation of a corresponding section of the blood vessel from the medical imaging data set;

For each blood vessel segment, extracting or determining one or more features from the representation of the corresponding section of the blood vessel, Performing a combining operation based on the extracted features for all of the blood vessel segments to obtain a global set of features which is based on the feature information of each blood vessel segment, and Determining the significance score based on the global set of features.

The partitioning of a blood vessel serves to simplify and standardize the further analysis by performing further steps with regard to a finite plurality of discrete blood vessel segments. A blood vessel system or blood vessel tree under analysis can be thus be divided into a plurality of discrete segments. The partitioning can be achieved in an automated fashion, e.g. by partitioning according to bifurcations, reduction in diameter or other criteria.

The representation of a blood vessel segment can be a graphical representation or a mathematical representation which is extracted from the medical imaging data. From such representation of a segment, one or more features can be extracted. These may be graphical features or mathematical features.

The feature may be determined within a trained function such as a neural network. As such, the feature may be represented within the trained function in an abstract form such as a sub-function, weighted edge, set of numerical coordinates, or similar.

The feature may e.g. relate to the geometry of the vessel walls of the respective blood vessel segment. In particular, the feature may be a feature indicative of the presence of a plaque, of the composition of a plaque, of the location of the plaque along the blood vessel centerline, of the extent of a plaque in the direction of the vessel center line (i.e. the length of a plaque), and/or of the severity of a plaque.

Examples of such feature can include:

information indicative of, consisting of, or comprising the diameter or cross-sectional area of the blood vessel at a given location, information indicative of, consisting of, or comprising the rate of change of the diameter or cross-sectional area of the blood vessel along the centerline direction, information indicative of, consisting of, or comprising the location and extent of a local maximum or minimum of the diameter or cross-sectional area of the blood vessel at a given location or within the respective blood vessel segment, information about the composition of a plaque, e.g. lipid plaque, calcified plaque, fibrotic plaque.

The plurality features extracted or determined (both terms can be used interchangeably in this context) for each blood vessel segment represent a set of features associated with each respective blood vessel segment. Thus, there is a plurality of sets of features for the respective plurality of blood vessel segments. This plurality of sets of features is combined into a global feature set for the entire plurality of blood vessels under analysis.

A significance score within the meaning of embodiments of the invention is a score which signifies a clinical information. A non-limiting list of examples is the likelihood or risk of having or developing a given clinical condition, the likelihood of benefiting from a given further diagnostic procedure or from a given therapy, the likelihood or risk of suffering adverse effects from a given therapy and similar information.

The step of generating output data by applying algorithmic operations to the input data may comprise generating output data by applying algorithmic operations to the input data by applying one or more trained functions (such as function trained by a machine learning algorithm) to the input data.

In its most general terms, at least one embodiment of the invention further relates to a system, comprising
 a first interface, configured for receiving input data,
 a second interface, configured for providing output data,
 a computation unit, configured for applying algorithmic operations to the input data, wherein the output data is generated.

In its most general terms, at least one embodiment of the invention further relates to a computer program comprising instructions which, when the program is executed by a computer cause the computer to carry out at least one embodiment of the method of invention in its most general terms.

In its most general terms, at least one embodiment of the invention further relates to a computer-readable medium comprising instructions which, when executed by a computer cause the computer to carry out at least one embodiment of the method of invention in its most general terms.

The invention in more particular terms and according to an example embodiment relates to the analysis of coronary arteries of a patient.

According to an example embodiment, the invention relates to a method of determining a significance score associated with a medical imaging dataset of a patient, the medical imaging dataset comprising image data of a region of a patient's anatomy including a plurality of coronary arteries; comprising:

Receiving the medical imaging data set;

Automatically partitioning each coronary artery of the plurality of coronary arteries into one or more coronary artery segments;

For each coronary artery segment, extracting a representation of a corresponding section of the coronary artery from the medical imaging data set;

For each coronary artery segment, extracting one or more features from the representation of the corresponding section of the coronary artery;

Performing a combining operation based on the extracted features for all of the coronary segments (of the the one or more coronary artery segments) to obtain a global set of features based on the quantitative information for each coronary segment;

Determining the significance score based on the global set of features; and

Outputting the determined significance score.

According to an example embodiment, the significance score is determined from a medical imaging data set. This medical imaging data set can be from any suitable imaging modality such as, for example CT or MR, and may be a raw data set a reconstructed image data set, or an image data set which has been further processed after reconstruction. For example, the medical imaging data set can comprise segmentation information of the coronary arteries.

The medical imaging data set comprises image data of a region of a patient's anatomy including a plurality of coronary arteries. This can include a section of the coronary artery tree or the entire coronary artery tree, e.g. comprising all the coronary arteries emanating from the aortic root.

According to an example embodiment, each coronary artery of the plurality of coronary arteries is portioned into one or more coronary artery segments. This can be achieved by an automated partitioning operation. Further analysis of the plurality of coronary arteries can then be performed for each coronary artery segment. The automatic partitioning operation of coronary artery segments can be performed e.g. by a further algorithmic operation which e.g. is based on detection of bifurcations or other anatomic landmarks in the coronary arteries. The automatic partitioning operation of coronary artery segments can also be e.g. performed by using a trained function, wherein an algorithm is trained to partition one or more coronary arteries into coronary artery segments.

According to an example embodiment, a representation of a section of the coronary artery corresponding to each segment is extracted from the medical imaging data set. This can be achieved by performing an algorithmic operation on the image data associated with each respective segment. The representation can be a data based representation such as a graphical representation or a mathematical representation. From such representation of a segment, one or more features can be extracted. These may be graphical features or mathematical features. The feature may be determined with a trained function such as a neural network. As such, the feature may be represented within the trained function in an abstract form such as a sub-function, weighted edge, set of numerical coordinates, or similar.

According to an example embodiment, a combining operation based on the extracted features for all of the coronary segments is performed to obtain a global set of features. This combining operation may be performed using a a trained function such as a neural network. For example the m features of n segments are combined to a global feature set for coronary artery segments 1, 2, ... n, the global feature set consisting of feature 1_combined to feature m_combined, each of the combined features 1_combined ... m_combined being based on the individual features 1 ... m of each coronary artery segments 1 ... n.

The combining operation may be implemented as a pooling operation, e.g. a max pooling operation. The advantage of using a combining operation, such as a pooling operation, is that the number of the number of parameters is reduced. This leads to the amount of computation in being reduced and to a control of overfitting. In a trained function, e.g. a neural network, the combining operation may be implemented as a pooling layer.

According to an example embodiment, the significance score is determined based on the global set of features; and in a further step the determined significance score is provided as output data. Outputting can be achieved via a dedicated interface and the determined significance score can thus be provided to a display, a printer, a memory, a network or in any other fashion suitable for inspection by a user, storage, or further processing.

According to a further aspect of an example embodiment, of the invention the medical imaging data set comprises information related to a respective plurality of centerlines of the plurality of coronary arteries.

Centerline information can be used for partitioning the coronary arteries.

According to a further aspect of an example embodiment, the one or more features is extracted by using a trained function.

In general, a trained function mimics cognitive functions that humans associate with other human minds. In particular, by training based on training data the trained function is able to adapt to new circumstances and to detect and extrapolate patterns.

In general, parameters of a trained function can be adapted via training. In particular, supervised training, semi-supervised training, unsupervised training, reinforcement learning and/or active learning can be used. Furthermore, representation learning (an alternative term is "feature learning") can be used. In particular, the parameters of the trained functions can be adapted iteratively by several steps of training.

In particular, a trained function can comprise a neural network, a support vector machine, a decision tree and/or a Bayesian network, and/or the trained function can be based on k-means clustering, Q-learning, genetic algorithms and/or association rules. In particular, a neural network can be a deep neural network, a convolutional neural network or a convolutional deep neural network. Furthermore, a neural network can be an adversarial network, a deep adversarial network and/or a generative adversarial network.

According to a further aspect of an example embodiment, the significance score is determined by using a trained function.

According to a further aspect of an example embodiment, the step of extracting a representation of a corresponding section of the coronary artery comprises creating an MPR image stack constructed by interpolating orthogonal planes for a plurality of points of the centerline of the corresponding section of the coronary artery. The term MPR stands for multi-planar reformation and is known in the art.

According to a further embodiment of the method of the invention, the step of automatically partitioning comprises partitioning each coronary artery of the plurality of coronary arteries into one or more coronary artery segments along the respective centerline of each coronary.

According to a further embodiment, a sub-significance score is determined for a selected individual coronary segment or a subgroup of coronary artery segments of a plurality of coronary segments. According to this embodiment of the invention further, and optionally, a coronary segment having the highest sub-significance score is identified. The sub-significance score can be based on the combined feature for each individual coronary segment. The sub-significance score thus can be used to identify the individual coronary segment which contributes most to the overall significance score. The sub-significance score may be displayed/outputted separately. For example, the sub-significance score can be displayed for each segment or for a subgroup of coronary artery segments, such as all coronary artery segments which together for one of the three major coronary arteries, RCA, LCX, LAD.

In further examples, only the most significant sub-significance score (i.e. from the individual coronary segment which contributes most to the overall significance score) or only sub significance score above a selected threshold is be displayed/outputted separately.

The additional displaying/outputting of significance scores, such as the most significant sub-significance score, makes it easier for a user to understand which blood vessel segment(s) contribute(s) most to the overall significance score, and thus provides valuable additional information to the user.

According to a further embodiment, the medical imaging dataset is a coronary CT angiography data set.

In particular, an embodiment of the invention further relates to a system for determining a significance score associated with a medical imaging dataset of a patient, the medical imaging dataset comprising image data of a region of a patient's anatomy including a plurality of coronary arteries; comprising:

A first interface for receiving unit for receiving the medical imaging data set;

A partitioning unit for automatically partitioning each coronary artery of the plurality of coronary arteries into one or more coronary artery segments;

A first extraction unit for extracting a representation of a corresponding section of the coronary artery from the medical imaging data set;

A second extraction unit for extracting a one or more features from the representation of the corresponding section of the coronary artery, A combining unit for performing a combining operation based on the extracted features for all of the coronary segments to obtain a global set of features based on the quantitative information for each coronary segment;

A calculation unit for determining the significance score based on the global set of features; and A second interface for providing the determined significance score.

Some or all of the aforementioned units can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

The term "unit" may be replaced with the term "circuit" or "module". The term "unit" may refer to, be part of, or include processor hardware (shared, dedicated, or group) that executes code and memory hardware (shared, dedicated, or group) that stores code executed by the processor hardware.

The units may be implemented in one control unit and each unit may include one or more interface circuits. Alternatively, the units may be implemented in a delocalized system, e.g. in a network. In some examples, the interface circuits may include wired or wireless interfaces that are connected to a local area network (LAN), the Internet, a wide area network (WAN), or combinations thereof. The functionality of any given unit of the present disclosure may be distributed among multiple modules that are connected via interface circuits. For example, multiple modules may allow load balancing. In a further example, a server (also known as remote, or cloud) module may accomplish some functionality on behalf of a client module.

An embodiment of the invention further relates to a computer program, which performs the steps of the methods of an embodiment of the invention if the computer program is executed on an evaluation device which may be or may comprise a computer or may be comprised by a computer.

An embodiment of the invention further relates to an electronically readable storage medium, on which the computer program of an embodiment of the invention is stored.

FIG. 1 shows an example schematic representation 100 of coronary arteries 103, 105 emanating from the aorta 101. The coronary arteries 103, 105 are shown partitioned into coronary segments 1 to 18. The partitioning may be achieved based upon other representations and into other segments. In particular, the representation shown in FIG. 1 is a 2D representation of a 3D vessel tree which has been truncated/limited to reduce complexity. Partitioning may be performed based on other representations, e.g. a 3D representation, and into other segments, e.g. more, less and/or different segments.

Figure 2:
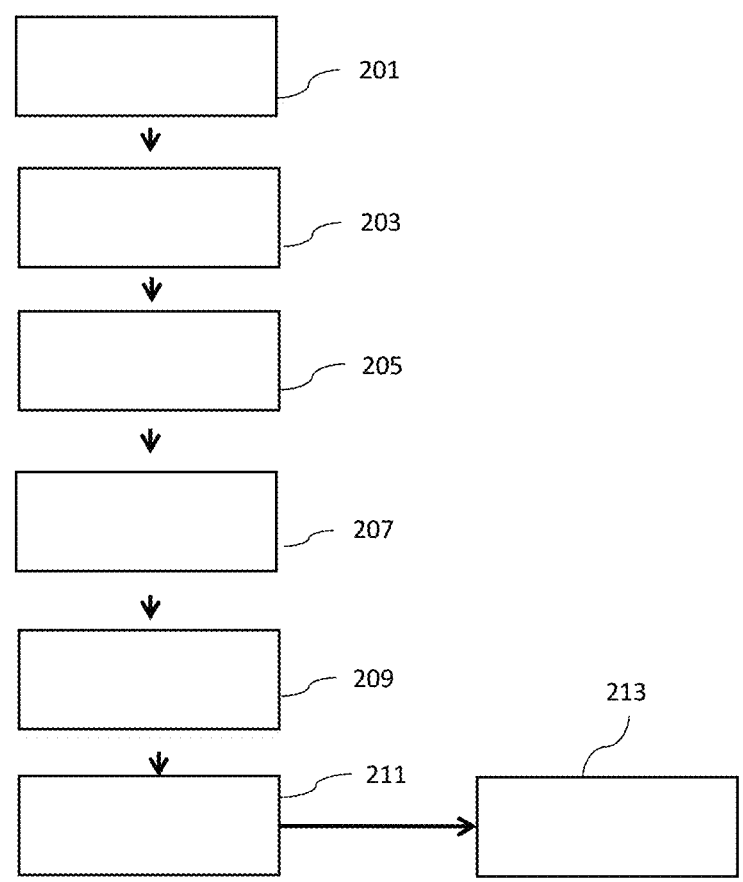
FIG. 2 shows a schematic representation of an embodiment of the method of the invention.

FIG. 2 shows a schematic representation of an embodiment of the method of the invention; comprising the steps of Receiving 201 a medical imaging data set of a patient;

Automatically partitioning 203 each coronary artery of the plurality of coronary arteries into one or more coronary artery segments, the medical imaging dataset comprising image data of a region of a patient's anatomy including a plurality of coronary arteries.

For each coronary artery segment, extracting 205 a representation of a corresponding section of the coronary artery from the medical imaging data set;

For each coronary artery segment, extracting 207 a one or more features from the representation of the corresponding section of the coronary artery, Performing a combining operation 209 based on the extracted features for all of the coronary segments to obtain a global set of features based on the quantitative information for each coronary segment, and Determining the significance score 211 based on the global set of features.

The determined significance score is then provided or outputted 213 as output data. Outputting 213 can be achieved via a dedicated interface and the determined significance score can thus be provided to a display, a printer, a memory, a network or in any other fashion suitable for inspection by a user, storage or further processing.

The example workflow shown in FIG. 2 is a linear workflow. It is noted that the individual steps may be performed also in parallel fashion and in iterative fashion wherein any intermediate or final outcome is used to repeat all or some selected steps for all or a selected sub-group of blood vessels, blood vessel segments, or features.

In an example workflow the coronary artery segments are partitioned along centerlines. From these, reformatted Multi-planar Reformatted (MPR) image stacks are extracted from the medical imaging data set by interpolating planes orthogonal to the centerline. These 3D stacks get resized to an intermediate length and processed by a trained function for feature extraction, e.g., a convolutional neural network. The features are combined to a global feature set.

For example, the segments 1 . . . n having the features a, b, c, d, . . . m. are combined such that a1 . . . n, b1 . . . n, etc. each are combined into, respectively, feature a_combined, b_combined, c_combined, d_combined, and a_combined, b_combined, c_combined, d_combined, . . . m_combined, wherein the combined features a_combined . . . m_combined together constitute the global feature set.

The features of the most severe lesion can be combined by filtering with a max pooling operation in order to then be classified by a classifier network or machine learning approach.

Advantageously, the centerlines of the coronary arteries are extracted. State-of-the-art methods for this task are already robust and accurate (e.g. Zheng, Y., Tek, H., & Funka-Lea, G. (2013), the entire contents of which are hereby incorporated herein by reference. Robust and accurate coronary artery centerline extraction in CTA by combining model-driven and data-driven approaches. International Conference on Medical Image Computing and Computer-Assisted Intervention, (pp. 74-81). Nagoya), the entire contents of which are hereby incorporated herein by reference.

In a second step, the coronary tree segment labels, as defined by the American Health Association (AHA), are automatically assigned to the corresponding coronary artery segments. For AHA labelling, see: Austen W G, Edwards J E, Frye R L, et al. A reporting system on patients evaluated for coronary artery disease. Report of the Ad Hoc Committee for Grading of Coronary Artery Disease, Council on Cardiovascular Surgery, American Heart Association. Circulation. 1975; 51(4 Suppl):5-40. doi:10.1161/01.cir.51.4.5), the entire contents of each of which are hereby incorporated herein by reference.

For each coronary artery segment, a suitable representation is extracted for processing. One option is to create an MPR image stack constructed by interpolating orthogonal planes for a plurality of centerline points. From the given representation the quantitative features are then extracted, e.g., by using an algorithm, e.g. with a trained function such as convolutional neural network. The extraction of the feature can in particular provide information about the geometry of the vessel walls of the respective blood vessel segment, e.g. to detect and/or characterize a plaque or stenosis. For example, analyzing the geometry of the vessel walls within the representation of the respective blood vessel segment, e.g. a local minimum or maximum of the diameter or cross-sectional area can be detected. Further, by way of example, additionally or alternatively a section with reduced diameter or cross-sectional area can be detected and its length can be determined which would be indicative of the length of a plaque or stenosis.

Subsequently, the highest activation for each feature along all segments is selected based on these characteristics by max-pooling.

Finally, according to an example embodiment, any classification method, e.g. a trained function, such as a multilayer perceptron or other machine learning algorithms, can be used to predict the significance score.

In an example embodiment the significance score is the "CAD-RADS" score.

In an example embodiment the significance score is a calcification score.

To summarize, in this example embodiment, the coronary artery centerlines and AHA segments are extracted. From these Multi-planar Reformatted (MPR) image stacks are extracted by interpolating planes orthogonal to the centerline. These 3D stacks get resized to an intermediate length and processed by a feature extraction algorithm, e.g., a convolutional neural network. The features of the most severe lesion get filtered by a max pooling operation in order to be classified by a classifier network or ML approach.

The main advantages of the proposed workflow and system are as follows:

Faster runtime due to independence from coronary artery lumen segmentation.

Robustness regarding possible outliers, i.e., falsely labelled segments, outliers especially during training.

The system can be used as a second opinion/safeguard for the medical practitioner suggesting potential treatment strategies and also indicates the AHA segments that mainly cause the overall assessment. The latter can be used to immediately look at the diseased segments and will eventually save time when reporting on a case.

The system allows fully automated quantitative CAD-RADS studies on large cohorts for e.g. identification of associations with blood parameters.

If tweaked to appropriate sensitivity and specificity values by an appropriate point of operation a fully automatic system for early identifying non-diseased patients is conceivable.

By reversing the MaxPooling operation using the activation maximization method, the most severe segment can be visualized allowing the prediction to be explainable. In this way, a sub-significance score is obtained and can be used to identify the individual coronary segment which contributes most to the overall significance score.

Since the location of the culprit lesion can be traced a differentiation between different modifiers (CAD-RADS 4A/4B) is possible.

In a proof-of-concept research study a data collection of 2.867 patients was evaluated. Based on the proposed workflow, obstructive from non-obstructive disease could be distinguished with an AUC, accuracy, sensitivity and specificity of 0.92, 0.86, 0.89, 0.80, which indicates the readiness of this approach for application as a screening method and/or a method to provide a so-called second opinion in a daily clinical scenario.

Figure 3:
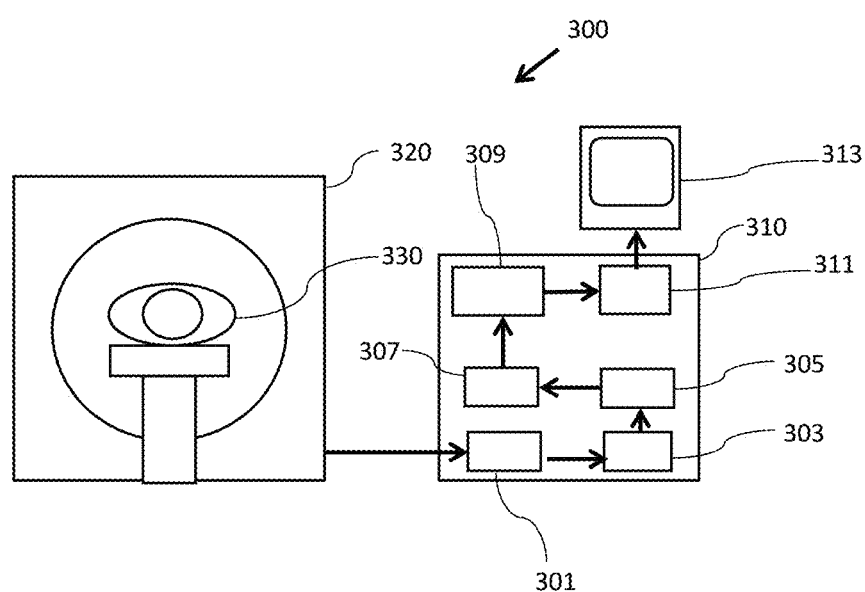
FIG. 3 shows a schematic representation of an embodiment of the system of the invention.

FIG. 3 shows a schematic representation of an embodiment of the system 300 of the invention. The system 300 comprises a medical imaging scanner 320, such as a CT or an MR scanner, for scanning a patient 330. The system 300 further comprises a control unit 310. A first interface 301 receives the medical imaging data set from the scanner 320. A partitioning unit 303 automatically partitions each coronary artery of the plurality of coronary arteries into one or more coronary artery segments. A first extraction unit 305 extracts a representation of a corresponding section of the coronary artery from the medical imaging data set. A second extraction unit 307 extracts a one or more features from the representation of the corresponding section of the coronary artery. A combining unit 309 for performing a combining operation based on the extracted features for all of the coronary segments to obtain a global set of features based on the quantitative information for each coronary segment. A calculation unit 311 for determines the significance score based on the global set of features. The determined significance score can then be output via a second interface 313, such as a display for inspection by a user or a storage unit or transmission unit for storage or further review and processing.

The example embodiments have been described for illustrative purposes. It will be obvious that the described features, steps and workflow may be varied in many ways. Such variations are not to be regarded as a departure from the scope of the present invention, and all such modifications as would be obvious to one skilled in the art are intended to be included within the scope of the following claims.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method of determining a significance score associated with a medical imaging dataset of a patient, the medical imaging dataset including image data of a plurality of coronary arteries of a-the patient, and the method comprising:
   automatically partitioning each among the plurality of coronary arteries, into one or more coronary artery segments to obtain a plurality of coronary artery segments;
   extracting a representation of a section of each among the plurality of coronary artery segments, from the medical imaging data-set to obtain a plurality of representations;
   extracting one or more features from each among the plurality of representations, each among the one or more features including quantitative information of a corresponding coronary artery among the plurality of coronary arteries;
   performing a combining operation based on the one or more features extracted for all among the plurality of representations to obtain a global set of features;
   determining the significance score based on the global set of features; and
   outputting the significance score.

2. The method of claim 1, wherein the extracting the one or more features extracts the one or more features using a trained function.

3. The method of claim 2, wherein the determining the significance score determines the significance score using a trained function.

4. The method of claim 2, wherein the medical imaging data-set includes information related to a plurality of centerlines respectively corresponding to the plurality of coronary arteries.

5. The method of claim 4, wherein the extracting the representation includes creating an MPR image stack corresponding to a first coronary artery among the plurality of coronary arteries, the MPR image stack being constructed by interpolating orthogonal planes for a plurality of points of a first centerline corresponding to a section of the first coronary artery.

6. The method of claim 4, wherein the automatically partitioning includes partitioning each respective coronary artery among the plurality of coronary arteries into one or more coronary artery segments along a centerline corresponding to the respective coronary artery.

7. The method of claim 1, wherein the determining the significance score determines the significance score using a trained function.

8. The method of claim 1, wherein the medical imaging data-set includes information related to a plurality of centerlines respectively corresponding to the plurality of coronary arteries.

9. The method of claim 8, wherein the extracting of the representation includes creating an MPR image stack corresponding to a first coronary artery among the plurality of coronary arteries, the MPR image stack being constructed by interpolating orthogonal planes for a plurality of points of a first centerline corresponding to a section of the first coronary artery.

10. The method of claim 9, wherein the automatically partitioning includes partitioning each respective coronary artery among the plurality of coronary arteries into one or more coronary artery segments along a centerline corresponding to the respective coronary artery.

11. The method of claim 8, wherein the automatically partitioning includes partitioning each respective coronary artery among the plurality of coronary arteries into one or more coronary artery segments along a centerline corresponding to the respective coronary artery.

12. The method of claim 1, further comprising:
    determining a sub-significance score for a first coronary artery segment among the plurality of coronary artery segments or a subgroup of coronary artery segments among the plurality of coronary artery segments.

13. The method of claim 12, further comprising:
    identifying a coronary artery segment among the plurality of coronary artery segments having a highest sub-significance score.

14. The method of claim 1, wherein the medical imaging dataset is a coronary CT angiography data-set.

15. A non-transitory computer program product, storing a computer program to perform the method of claim 1 based on the computer program being executed on by at least one processor.

16. A non-transitory electronically readable storage medium, storing a computer program to perform the method of claim 1 based on the computer program being executed by at least one processor.

17. The method of claim 1, wherein the global set of features includes a plurality of feature groupings, each feature grouping including quantitative information for a different feature of all among the plurality of coronary artery segments, the different feature being among the one or more features.

18. The method of claim 1, wherein the determining the significance score includes determining a highest activation for each among the one or more features across all among the plurality of coronary artery segments.

19. The method of claim 1, wherein the combining operation is a max pooling operation.

20. A system for determining a significance score associated with a medical imaging dataset of a patient, the medical imaging dataset including image data of a plurality of coronary arteries of the patient, and the system comprising:
    processing circuitry configured to
        automatically partition each among the plurality of coronary arteries into one or more coronary artery segments to obtain a plurality of coronary artery segments;

extract a representation of a section of each among the plurality of coronary artery segments from the medical imaging data-set to obtain a plurality of representations;

extract one or more features from each among the plurality of representations, each among the one or more features including quantitative information of a corresponding coronary artery among the plurality of coronary arteries;

perform a combining operation, based on the one or more features extracted for all among the plurality of representations to obtain a global set of features;

determine the significance score based on the global set of features; and provide the significance score.

* * * * *